United States Patent [19]

Sarantakis

[11] 4,093,609

[45] June 6, 1978

[54] SOMATOSTATIN SYNTHESIS

[75] Inventor: Dimitrios Sarantakis, West Chester, Pa.

[73] Assignee: American Home Products Corporation, New York, N.Y.

[21] Appl. No.: 749,499

[22] Filed: Dec. 10, 1976

[51] Int. Cl.$^2$ .................................................. C07C 103/52
[52] U.S. Cl. ............................................... 260/112.5 S
[58] Field of Search ....................... 260/112.5 S, 112.7

[56] References Cited

U.S. PATENT DOCUMENTS 3,917,578  11/1975  Immer et al. .................. 260/112.5 S
3,917,581  11/1975  Immer et al. .................. 260/112.5 S

OTHER PUBLICATIONS

J. Rivier; J. Am. Chem. Soc., 96, 1974, 2986–2992.
E. Wolters, et al.; J. Org. Chem., 39, No. 23, 1974, 3388–3392.

*Primary Examiner*—Delbert R. Phillips
*Attorney, Agent, or Firm*—Richard K. Jackson

[57] ABSTRACT

A mixed solid phase-solution phase synthesis for somatostatin which combines the speed of conventional solid phase synthesis with the advantage of solution phase isolation and purification techniques.

3 Claims, No Drawings

SOMATOSTATIN SYNTHESIS

BACKGROUND OF THE INVENTION

The first solid phase synthesis of somatostatin was reported by Rivier et al., *C.R. Acad. Sc. Paris*, D 276 2737 (1973) and Rivier, *J.A.C.S.* 96 2986 (1974).

The first in solution, conventional synthesis of somatostatin was reported by Sarantakis and McKinley, *BBRC* 54, 882 (1973). A conventional synthesis was reported by Immer et al., *Helv. Chim. Acta* 57, 730 (1974) and also by Fujii et al., *Chem. Pharm. Bull.* 23 1596 (1975). Veber, "Peptides, Chemistry, Structure, Biology" Ed. Walter and Meienhofer, p. 307 (1975) and Giori et al., ibid, p. 859.

DESCRIPTION OF THE INVENTION

Synthesis of somatostatin by the solid phase method is a relatively rapid although imprecise procedure in which purification at each stage of amino acid introduction into the polypeptide is very difficult, requiring repeated treatment of the resin bound polypeptide with organic solvents to remove reagents. In addition, the analytical techniques available for determining success at each reaction stage are quite limited because of the presence of the resin. Likewise, the final complete deprotection and removal of the resin from the polypeptide is a time consuming operation because of the size of the resin and its insolubility.

To avoid these problems, the present invention provides a mixed solid phase-solution phase procedure for producing somatostatin, which is substantially as fast as the solid phase method while providing for the isolation and purification of key intermediates, which are then coupled by solution techniques, minimizing the use of acidic treatments of labile groups such as Trp and Cys.

In essence, the process of this invention is conducted by producing the fully protected octapeptide (R)Phe-Phe-Trp-Lys(R)-Thr(R)-Phe-Thr(R)-Ser(R)-O-Resin in the conventional solid phase manner. The polypeptide is removed from the resin and simultaneously converted to the hydrazide by reaction with anhydrous hydrazine. The fully protected hydrazide is condensed with Cys(SR)(OR). The α-amino protecting group of (R)Phe is removed and (R)Asn is coupled N-terminally. The α-amino protecting group of (R)Asn is removed and the decapeptide is condensed with (R)Ala-Gly-Cys-Lys(R)-OH to yield the fully protected linear somatostatin which is deprotected and oxidized to afford somatostatin in good yield comparable to that obtained in conventional solid phase preparations.

Schematically, the process of this invention is depicted as follows, where the abbreviations employed for the specific protecting groups are: Boc=t-butoxycarbonyl, ClZ=2-chlorobenzyloxycarbonyl, Z=benzyloxycarbonyl, Bzl=benzyl, MBzl=p-methoxybenzyl; NP=p-nitrophenyl, HOBTA=N-hydroxybenzotriazole, and TFA=trifluoroacetic acid.

Synthetic Scheme

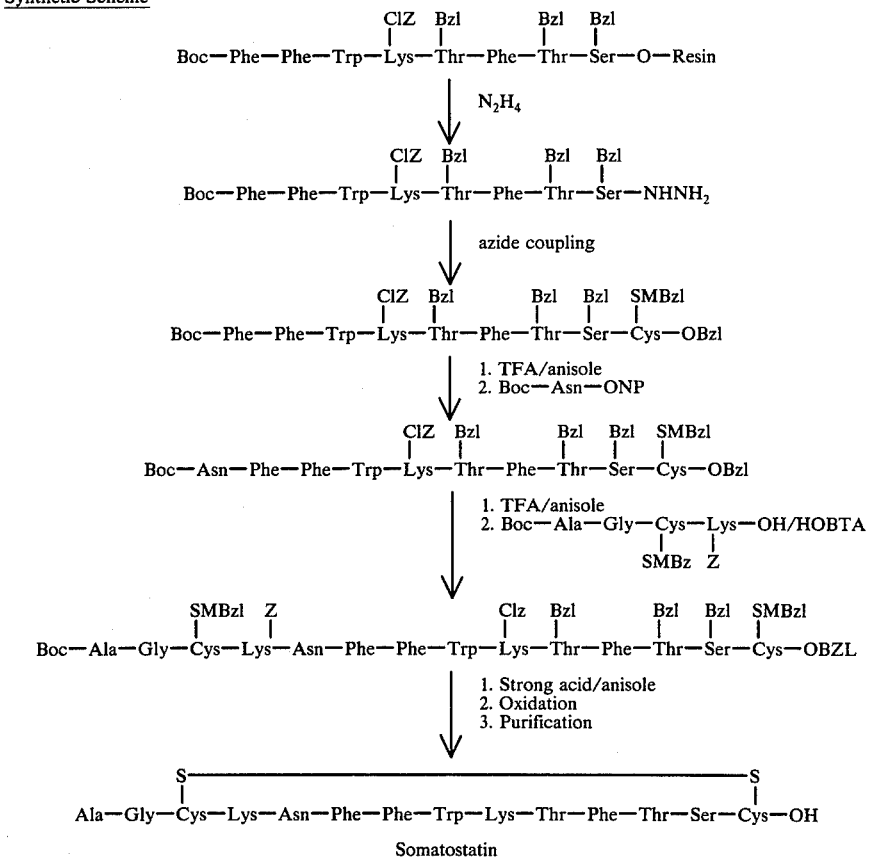

Somatostatin

The following example, presented for purpose of illustration only, is not to be construed as limiting in regard to the specific protecting groups employed. The protecting groups are designated R throughout the specification and claims, without further dignity, because it is to be understood that the selection of desired protecting groups for the various amino acid moieties is well within the skill of the art as demonstrated by the references cited in the background for the invention. For example, the S-protecting groups may be acetamidomethyl, trityl, carbamoyl, thioethyl, thio-tert-butyl, etc. Likewise the applicable O and N protecting groups are readily as certainable from the prior art. The oxidation step for cyclization of somatostatin may be performed by air oxidation, iodine in methanol, $HgCl_2$ followed by diiodoethane oxidation, potassium ferricycanide oxidation, and the like.

EXAMPLE I tert-Butyloxycarbonyl-L-phenylalanyl-L-phenylalanyl-L-tryptophyl-ε-2-chlorobenzyloxycarbonyl-L-lysyl-O-benzyl-L-threonyl-L-phenylalanyl-O-benzyl-L-threonyl-O-benzyl-L-seryl hydrazide Chloromethylated polystyrene resin (Lab Systems, Inc.) 10 g. was esterified with BOC-Ser(Bzl)-OH according to Gisin, *Helv. Chim. Acta.* 56, 1976 (1973). The amino acid resin was analyzed by quantitative amino acid analysis and was found to contain 0.40 mmoles serine per gram. This polymeric ester was treated according to Schedule A for the incorporation of Boc-Thr(Bzl)-OH, Boc-Phe-OH, Boc-Thr(Bzl)-OH, Boc-Lys(ClZ)-OH, Boc-Trp-OH, Boc-Phe-OH, and Boc-Phe-OH.

Schedule A 1. wash with $CH_2Cl_2 \times 3$
2. treat with TFA-$CH_2Cl_2$-DTE (1:2:0.5%) for 5 min.
3. treat with TFA-$CH_2Cl_2$-DTE (1:2:0.5%) for 25 min.
4. wash with $CH_2Cl_2 \times 3$
5. wash with DMF
6. Treat with 12% TEA in DMF twice for 3 min.
7. wash with DMF
8. wash with $Ch_2Cl_2 \times 3$
9. treat with 4 equivalents of the corresponding amino acid derivative in $CH_2Cl_2$-DMF and 4 equivalents of N-hydroxy-benzotriazole and stir for 5 min.
10. Add in two portions 5 equivalents of DIC dissolved in $CH_2Cl_2$ and over a period of 30 minutes. Reaction time 12–18 hours.
11. wash with DMF $\times$ 3
12. wash with $CH_2Cl_2 \times 3$
13. test ninhydrin reaction according to Kaiser et al., *Annal. Biochem.* 34, 595 (1970). In case of incomplete reaction repeat lines 9 to 13 as above.

The above peptidoresin was suspended in 150 ml. pure DMF and then treated with 50 equivalents of anhydrous hydrazine for 5 hours at room temperature. The mixture was filtered and the filtrate was evaporated to a small volume in vacuo. The residue was treated with an excess of water to give a white precipitate which was dissolved in DMF and precipitated with water twice. This solid was dried over $P_2O_5$ to obtain the title compound.

EXAMPLE II tert-Butyloxycarbonyl-L-phenylalanyl-L-phenylalanyl-L-tryptophyl-ε-2-chlorobenzyloxycarbonyl-L-lysyl-O-benzyl-L-threonyl-L-phenylalanyl-O-benzyl-L-threonyl-O-benzyl-L-seryl-S-P-methoxylbenzyl-L-cysteine benzyl ester The protected octapeptide hydrazide of the previous example (12.9 g.) was dissolved in DMF (ca. 100 ml.) cooled at −15° C. and treated with 4.5 N/HCl in EtOAc (3 equivalents) followed by n-isoamylnitrite (1.5 equivalents) The solution was stirred at −15°C. for 10 minutes then neutralized with triethylamine until pH 7.5 and a solution of Cys(SMBzl)OBzl p-toluenesulfonic acid salt (5.1 g.) in DMF neutralized with triethylamine was added. The mixture was stirred for one hour at −15°C. then for 2 days in the cold room (5°C.) after which time it was filtered and the filtrate evaporated to dryness. The residue was treated with a dilute aqueous solution of citric acid to give a white solid, filtered and washed with water then dried over $P_2O_5$. This solid was chromatographed through a column of silica gel and eluted with a mixture of chloroform-methanol 25:1 (v:v) to give a white solid, 15.3 g. The compound can be chromatographed through a column of Sephadex LH-20 and eluted with chloroform-methanol or DMF.

EXAMPLE III tert-Butyloxycarbonyl-L-asparaginyl-L-phenylalanyl-L-phenylalanyl-L-tryptophyl-ε-2-chlorobenzyloxycarbonyl-L-lysyl-O-benzyl-L-threonyl-L-phenylalanyl-O-benzyl-L-threonyl-O-benzyl-L-seryl-S-p-methoxybenzyl-L-cysteine benzyl ester.

The protected nonapeptide ester of the previous example (14.5 g.) was treated with 150 ml. trifluoroacetic acid in the presence of anisole (25 ml.) for 40 minutes at room temperature. The solution was evaporated to dryness and the residue was treated with an excess of ether to give an off white solid which was filtered and dried overnight in vacuo and over $P_2O_5$ and KOH. This solid was dissolved in DMF (150 ml.) neutralized with triethylamine and mixed with BOC-Asn-ONP (1.5 equivalents) in the presence of N-hydroxybenzotriazole as catalyst (gl. acetic acid can be used instead of the above catalyst). The solution was left to stand for 3 days then evaporated to a very small volume, it was treated with an excess of water to give a white solid which was dried over $P_2O_5$. This solid was washed well with absolute ethanol to give the title compound, 13 g., mp. 220°–224°.

EXAMPLE IV tert-Butyloxycarbonyl-L-alanyl-glycyl-S-p-methoxybenzyl-L-cysteinyl-ε-benzyloxycarbonyl-L-lysyl-L-asparaginyl-L-phenylalanyl-L-phenylalanyl-L-tryptophyl-ε-2-chlorobenzyloxycarbonyl-L-lysyl-O-benzyl-L-threonyl-L-phenylalanyl-O-benzyl-L-threonyl-O-benzyl-L-seryl-S-p-methoxybenzyl-L-cysteine benzyl ester.

The protected decapeptide of the previous example (1.8 g.) was dissolved in trifluoroacetic acid (50 ml.) containing some anisole (5 ml.), stirred for 40 minutes and evaporated to dryness. The residue was treated with an excess of ether to give a solid (1.18 g. which was dried over $P_2O_5$ and KOH.

This solid was dissolved in DMF (10 ml.) treated with triethylamine until pH 7, mixed with N-hydroxybenzotriazole (2 equivalents) and the mixture cooled in an ice-bath. A solution of BOC-Ala-Gly-Cys(SMBzl)-Lys(Z)-OH (preparation of this compound is described in U.S. Pat. No. 3,862,925 example I) (slight excess) in DMF was added and then dicyclohexylcarbodiimide (slight excess). The solution was stirred for two hours in the cold then for 24 hours at room temperature. The dicyclohexylurea which separated was filtered and the filtrate evaporated to a small volume. The residue was treated with water to give a solid which was filtered and washed with absolute ethanol, then dried over P₂O₅ to give a white solid, 1 g.

EXAMPLE V

L-Alanyl-glycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine (1 14 cyclic) disulfide (Somatostatin)

The protected tetradecapeptide of the previous example was treated as in U.S. Pat. No. 3,862,925, example XIV to afford pure somatostatin.

What is claimed is:

1. In a solution phase synthesis of somatostatin wherein successive amino acid residues are coupled N-terminally to a preceding peptide fragment followed ultimately by complete deprotection of the tetradecapeptide and oxidation to produce the 3-14 disulfide bond, the improvement which comprises:
   (a) preforming by solid phase synthesis the compound (R)Phe-Phe-Trp-Lys(R)-Thr(R)-Phe-Thr(R)-Ser(R)-O-Resin
   (b) removing the fully protected octapeptide from the Resin by reaction with hydrazine;
   (c) coupling the octapeptide hydrazide with Cys(R)(OR) by the azide method and subsequently
   (d) completing the N-terminal elongation of the peptide chain by the solution method.

2. The improvement of claim 1 in which step (d) is accomplished by coupling (R)Asn O-p-nitrophenyl ester N-terminally followed by coupling of (R)Ala-Gly-Cys-Lys(R)OH.

3. A process for the production of somatostatin which comprises
   (a) condensing α-amino and hydroxy protected Ser with a chloromethylated or hydroxymethylated polystyrene resin support;
   (b) removing the α-amino protecting group of Ser(R)-OCH₂ Resin;
   (c) serially coupling N-terminally the appropriately protected amino acid with sequential removal of the α-amino protecting group to obtain a compound of the formula: (R)Phe-Phe-Trp-Lys(R)-Thr(R)-Phe-Thr(R)-Ser(R)-O-Resin
   (d) removing the octapeptide from the resin with hydrazine to produce the octapeptide hydrazide; and completing the synthesis by the solution method as follows:
   (e) coupling Cys(R)(OR) C-terminally by the azide method;
   (f) removing the α-amino protecting group of Phe;
   (g) coupling (R)Asn N-terminally as the activated p-nitrophenyl ester;
   (h) removing the α-amino group of Asn;
   (i) coupling (R)Ala-Gly-Cys-Lys(R)OH by the dicyclohexylcarbodiimide-hydroxybenzotriazole method;
   (j) completely deprotecting the tetradecapeptide and
   (k) oxidizing the linear tetradecapeptide to form the 3-14 disulfide ring.

* * * * *